(12) United States Patent
Torii et al.

(10) Patent No.: US 7,879,924 B2
(45) Date of Patent: Feb. 1, 2011

(54) DENTAL COMPOSITE RESIN CEMENT, DENTAL PRIMER AND DENTAL ADHESIVE KIT CONTAINING THEM

(75) Inventors: Keisuke Torii, Kyoto (JP); Hisaki Tanaka, Kyoto (JP); Toshihide Fujii, Higashiyama-ku (JP); Yoshiaki Kohro, Kyoto (JP); Mikito Deguti, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 265 days.

(21) Appl. No.: 11/815,098

(22) PCT Filed: Feb. 3, 2006

(86) PCT No.: PCT/JP2006/301845

§ 371 (c)(1),
(2), (4) Date: Jul. 30, 2007

(87) PCT Pub. No.: WO2007/088628

PCT Pub. Date: Aug. 9, 2007

(65) Prior Publication Data

US 2009/0048366 A1    Feb. 19, 2009

(51) Int. Cl.
A61K 6/083 (2006.01)
A61K 6/08 (2006.01)
A61C 5/00 (2006.01)
C08F 30/02 (2006.01)
C08F 230/02 (2006.01)
C08F 2/50 (2006.01)
C07F 9/30 (2006.01)

(52) U.S. Cl. .................. 523/116; 523/115; 433/226; 433/228.1; 106/35; 526/274; 526/278; 522/14; 522/24; 522/171; 558/214

(58) Field of Classification Search ............... 523/113, 523/115, 116, 118; 433/228.1, 226; 106/35; 526/274, 278; 522/14, 24, 171; 558/214
See application file for complete search history.

(56) References Cited

U.S. PATENT DOCUMENTS

| | | | |
|---|---|---|---|
| 5,264,513 A | 11/1993 | Ikemura et al. | |
| 6,191,191 B1 * | 2/2001 | Harada et al. | 523/115 |
| 6,583,197 B1 * | 6/2003 | Wada et al. | 522/84 |
| 6,869,984 B2 | 3/2005 | Kawashima et al. | |
| 2003/0083398 A1 * | 5/2003 | Kawashima et al. | 523/115 |
| 2004/0077746 A1 * | 4/2004 | Takeshita et al. | 523/116 |
| 2004/0235981 A1 * | 11/2004 | Qian | 523/115 |
| 2007/0225443 A1 * | 9/2007 | Skelskey et al. | 525/107 |

FOREIGN PATENT DOCUMENTS

| | | |
|---|---|---|
| CA | 2065472 | 10/1993 |
| JP | 3-240712 | 10/1991 |
| JP | 4-8368 | 1/1992 |
| JP | 2001-72523 | 3/2001 |
| JP | 2003-12430 | 1/2003 |
| JP | 2005-289961 | 10/2005 |
| JP | 289961 | 10/2005 |

* cited by examiner

Primary Examiner—Mark Eashoo
Assistant Examiner—Michael Pepitone
(74) Attorney, Agent, or Firm—Novak Druce & Quigg LLP

(57) ABSTRACT

The present invention provides a dental resin cement which is excellent in a mechanical strength, workability and storage stability, and a dental primer which significantly improves adhesiveness of the dental resin cement both to enamel and dentin of a tooth. According to the present invention, a salt of barbituric acid is used as a polymerization initiator in the dual-cure two-paste type dental resin cement being excellent in workability and storage stability to improve the storage stability, and a primer containing barbituric acid and amine is applied to a surface of a tooth to significantly improve adhesiveness of the dental resin cement both to enamel and dentin of teeth.

4 Claims, No Drawings

DENTAL COMPOSITE RESIN CEMENT, DENTAL PRIMER AND DENTAL ADHESIVE KIT CONTAINING THEM

TECHNICAL FIELD OF THE INVENTION

The present invention relates to a two-paste type dental composite resin cement for adhering dental prosthetic materials such as metals, ceramics, polymer materials and the like to a matrix of bio hard tissues such as enamel and dentin of natural teeth and the like. More specifically, the composite resin cement of the present invention is excellent in workability and storage stability.

In addition, the present invention relates to a dental primer which improves adhesion between the two-paste type dental composite resin cement and the matrix of bio hard tissues such as enamel and dentin of natural teeth.

Further, the present invention also provides a dental adhesive kit containing the two-paste type dental composite resin cement and the dental primer.

BACKGROUND ART

Generally, teeth receiving a relatively intensive damage by caries and the like are restored by adhering crown, bridge, inlay, onlay and the like which consist of ceramics, polymer materials, or metal materials by using a resin cement.

Resin cements are required to have a sufficient mechanical strength and a sufficient adhesion strength to dental hard tissues. Otherwise, it is possible that a resin cement comes out during long use in severe oral circumstances and that gaps form at an interface between a resin cement and dental materials and bacteria come in by the gaps to deteriorate dental pulp.

Resin cements may be categorized into a poly(methyl methacrylate) (PMMA) type and a composite type. The PMMA type resin cement comprises PMMA and methyl methacrylate and it has a poor mechanical strength but is excellent in impact resistivity and adhesiveness to a variety of materials. On the other hand, the composite type resin cement comprises dental polymerized monomers and organic composite materials and filler such as glass, silica and the like, and is excellent in adhesion as well as material properties after curing such as a flexural strength, a compressive strength and the like. Therefore, clinic dentists make proper use of two types of resin cements depending on purposes and cases.

Recently, resin cements are highly required to use as adhesive for dental prosthetic materials with esthetics. Resin cements for this purpose should have a high mechanical strength. Therefore, in this field, a composite type resin cement is used because it has an excellent mechanical strength. Such a composite type resin cement usually has a filler content of 50% by weight or higher in order to achieve a high mechanical strength.

As for a conventional composite type resin cement, a powder-liquid type has been mainly used, in which, for example, filler (cement powder) and a monomer solution are provided in a two-package type and the powder and the liquid are mixed just prior to use.

Japanese Patent No. 1784478 [Patent Document 1] discloses in its specification that a dental restoration composition containing radical polymerizable monomers such as methyl methacrylate and the like and curing agents including organic peroxide, amine, a barbituric acid derivative, and acid anhydride or phosphate.

However, such a powder-liquid type resin cement is not clinically satisfactory from a viewpoint of workability in mixing.

Accordingly, a requirement for a two-paste type resin cement is increasing, in which two previously-prepared pastes are mixed in order to avoid complexity in mixing powder and liquid. This two-paste type resin cement is a preferable form for clinicians because mixing two pastes reduces a mixing time and person to person variation comparing to mixing powder and liquid.

Mechanisms for curing a resin cement include chemical polymerization and photo polymerization. When a resin cement is cured only by chemical polymerization, a surface curing degree of the resin cement is low and a non-polymerized layer forms on the surface where the cement exposes because polymerization is inhibited by oxygen in the air. On the other hand, when the resin cement is cured only by photo polymerization, in cases where prosthetic materials of low light transmittance such as crowns are adhered or cavities occurred by caries are filled, it is difficult to cure resin cement sufficiently because parts where light can not reach exist.

Therefore, a dual-cure type resin cement becomes popular in which photo polymerization as well as chemical polymerization occurs in order to achieve sufficient polymerization even in parts where light cannot reach so as to use for prosthetic materials of low light transmittance while curing at a surface part is promoted by photopolymerization by light radiation.

Such a dual-cure type resin cement may contain a variety of polymerizable monomers and reactive components such as red-ox type polymerization initiators and the like.

For a conventional powder-liquid type of resin cement, there is no concern about reaction among a variety of components as far as they are packed prior to mixing. However, for a two-paste type composite resin cement, it is possible that a variety of components react in pastes to reduce storage stability of the pastes.

Accordingly, in a field of dental prosthetic and restoration, it is recently desired to invest the dual-cure two-paste type composite resin, which is excellent in mechanical strength and workability, with storage stability.

In order to improve adhesiveness of a composite resin cement to bio hard tissues such as tooth substances, primers pre-treating a tooth surface have been used prior to application of composite resin cement to the tooth substances.

Japanese Patent No. 2670522 [Patent Document 2] discloses in its specification a primer compound used for hard tissues such as tooth substances. This primer demineralizes a tooth to make a surface tooth rough by acid etching. An adhesion mechanism is supposed that resin cement penetrates into fine structures of the rough surface and the resin cement cures in this state to form mechanical connection between the resin cement and the tooth surface.

As described above, demineralization by acid etching damages tooth substances. Further, a dental hard tissue comprises enamel and dentin, and adhesiveness to both enamel and dentin is clinically required but it is not considered that an adhesion strength of a resin cement to a surface of hydrophilic dentin is sufficient.

Japanese Patent No. 2634276 [Patent Document 3] discloses in its specification a primer improving adhesiveness of a resin cement both to enamel and dentin without a treatment which will damages a tooth surface such as acid etching and the like.

This primer comprises a polymerizable compound containing acidic groups such as a carboxyl group and a phosphate group and the like.

Japanese Patent No. 2865794 [Patent Document 4] discloses in its specification an adhesive composition comprising: (a) a (meth)acrylic ester derivative containing a phosphonate group represented by the general formula (I):

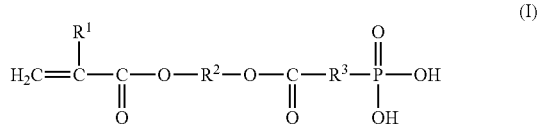

wherein $R^1$ is a hydrogen atom or a methyl group, $R^2$ is an alkylene group having a carbon number of 5 to 10, $R^3$ is an alkylene group having a carbon number of 1 to 6 as a polymerizable compound containing acidic groups; (b) at least one kind of radical polymerizable monomers; (c) at least one kind of polymerization initiators. When the phosphonate group contained in the (meth)acrylic acid ester derivative is applied on tooth substances, the phosphonate group chemically connects with calcium components in the tooth substances and, consequently polymerizable groups are attached on a surface of the tooth substances. By copolymerizing these polymerizable groups and other polymerizable monomers in the resin cement, adhesiveness of the resin cement to the tooth substances may be improved.

The adhesive composition includes a dental adhesive composition, a dental compound filler, a hard resin adhesive for crowns and the like. For example, a powder material such as silica and the like may be added to the above composition to manufacture an adhesive resin cement.

Japan Patent No. 3449755 [Patent Document 5] discloses in its specification a primer composition comprising: (a) a vinyl compound containing acidic groups such as a phosphonate group and the like as a polymerizable compound containing acidic groups; (b) a water soluble vinyl compound containing hydroxide groups; (c) water; (d) an aromatic sulfinic acid salt and (e) an aromatic secondary or tertiary amine. The primer compound is provided as an adhesive kit with a specific acrylic adhesive, wherein acrylic monomers are used as the specific acrylic adhesive.

According to the adhesive kit, a high adhesion strength is achieved to enamel and dentin of tooth. However, when a vinyl compound containing acidic groups is used in a resin cement, there is a problem that polymerization curing is suppressed and sufficiently cured material cannot be obtained.

JP 10-251115A [Patent Document 6] discloses in its specification a dental primer mainly comprising (A) a phosphate group-containing polymerizable monomer as a polymerizable monomer containing acidic groups; (B) a multi-valent carboxylate group-containing polymerizable monomer and (C) water.

According to the dental primer, adhesion strength of 20 MPa or higher may be achieved both to dentin and enamel.

JP 2000-204010A [Patent Document 7] discloses in the Specification a primer compound comprising (A) a sulfonate group-containing polymerizable monomer as a polymerizable compound containing acidic groups; (B) a water soluble polymerizable monomer and (C) water. The primer compound is provided as a dental adhesive kit with a specific adhesive, wherein acidic phosphoric acid ester multi-functional polymerizable monomers are used as the specific adhesive.

According to the dental adhesive kit, an adhesion strength of 20 MPa or higher may be achieved both to dentin and enamel.

However, with respect to any one of dental primer compositions disclosed in Patent Documents 4 to 7, it is not obvious whether sufficient adhesion strength can be achieved both to enamel and dentin when they are used in a two-paste type dual cure composite resin cement.

[Patent Document 1] Japanese Patent No. 1784478
[Patent Document 2] Japanese Patent No. 2670522
[Patent Document 3] Japanese Patent No. 2634276
[Patent Document 4] Japanese Patent No. 2865794
[Patent Document 5] Japan Patent No. 3449755
[Patent Document 6] JP 10-251115A
[Patent Document 7] JP 2000-204010A

DISCLOSURE OF THE INVENTION

Problem to be solved by the Invention

With considering the above problem, the present invention provides a two-paste type dual-cure dental composite resin cement which is excellent in a mechanical strength, workability and storage stability, and which may be used for prosthetic restorative materials of low light transmittance, and a dental primer which significantly improves adhesiveness of the dental composite resin cement both to enamel and dentin of a tooth.

Means for Solving the Problem

The present invention provides, as a dental resin cement composition excellent in workability and storage stability, a two-paste type dental composite resin cement comprising:

a component (a) radical polymerizable monomer;

a component (b) fluoroaluminosilicate glass filler;

a component (c)-(1) organic peroxide;

a component (c)-(2) alkali metal salt or an alkaline earth metal salt of barbituric acid;

a component (c)-(3) photopolymerization initiator;

a component (c)-(4) aromatic secondary or tertiary amine; and a component (d) shelf life stabilizer, and is free of water.

The two-paste type composite resin cement according to the present invention comprises, based on 100 parts by weight of the whole resin cement formulation, 20.0 to 45.0 parts by weight of the component (a) radical polymerizable monomer;

50.0 to 80.0 parts by weight of the component (b) fluoroaluminosilicate glass filler;

20.0 to 45.0 parts by weight of the component (c)-(1) organic peroxide;

0.1 to 0.5 parts by weight of the component (c)-(2) alkali metal salt or alkaline earth metal salt of barbituric acids;

0.05 to 1.0 parts by weight of the component (c)-(3) photopolymerization initiator;

0.1 to 0.5 parts by weight of the component (c)-(4) aromatic secondary or tertiary amine; and 0.02 to 0.2 parts by weight of the component (d) shelf life stabilizer, provided that a sum of the respective components does not exceed 100 parts by weight.

In addition, the present invention provides a dental primer as a dental primer improving adhesion strength of the above-mentioned resin cement to dental hard tissues including enamel and dentin, comprising:

a component (e) water;
a component (f) polymerizable monomer represented by the general formula (I):

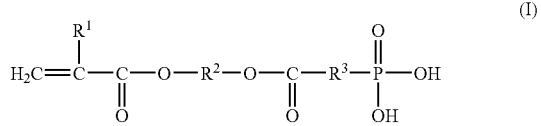

wherein $R^1$ is a hydrogen atom or a methyl group, $R^2$ is an alkylene group having a carbon number of 5 to 10, $R^3$ is an alkylene group having a carbon number of 1 to 6;
a component (g) polymerizable monomer containing a dibasic acid carboxyl group or acid anhydride;
a component (h) barbituric acid; and
a component (i) amine.

The two-paste type composite resin cement according to the present invention comprises, based on 100 weight % of the whole resin cement formulation,
20.0 to 60.0 weight % of the component (e) water;
2.0 to 10.0 weight % of the component (f) polymerizable monomer represented by the general formula (I);
5.0 to 25.0 weight % of the component (g) polymerizable monomer containing a dibasic acid carboxyl group or acid anhydride;
1.0 to 5.0 weight % of the component (h) barbituric acid; and
1.0 to 5.0 weight % of the component (i) amine, provided that a sum of the respective components does not exceed 100 weight %.

Further, the present invention also provides a dental adhesive kit containing the two-paste type dental composite resin cement and the dental primer in order to maintain workability and storage stability of two-paste type composite resin cement and to invest the composite resin cement with strong adhesion and high resistance without carrying out any treatment such as acid treatment and the like on a matrix of bio hard tissues, specifically enamel and dentin.

The component (a) radical polymerizable monomer used in the present invention is not limited, but includes vinyl acetate, acrylonitrile, styrene, (meth)acrylic acid, (meth)acrylate such as methyl (meth)acrylate, ethyl (meth)acrylate and the like, and their derivatives in which an alkali side chain is substituted with a hydroxide group or halogen, methoxydiethylene glycol (meth)acrylate, methoxypolyethylene glycol (meth)acrylate, ethylene glycol di(meth)acrylate, triethylene glycol di(meth)acrylate, polyethylene glycol di(meth)acrylate, propylene glycol (meth)acrylate, polypropylene glycol di(meth)acrylate, neopentyl glycol di(meth)acrylate, 2,2'-bis(4-(meth)acryloxypropoxyphenyl)propane, 2,2'-bis(4-(meth)acryloxyethoxyphenyl)propane, 2,2'-bis[4-(3-(meth)acryloyloxy-2-hydroxypropoxy)phenyl]propane, bisphenol A diglycidyl (meth)acrylate, diallyl phthalate, triallyl cyanurate, trimethylolpropane tri(meth)acrylate, trimethylolethane tri(meth)acrylate, tetramethylolmethane tetra(meth)acrylate, epoxy-(meth)acrylate and urethane dimethacrylate (UDMA) such as di-2-(meth)acryloyloxyethyl-2,2,4-trimethylhexamethylene dicarbamate or a polymerizable monomer containing a silanol group, such as γ-methacryloyloxypropylmethoxysilane and the like.

These radical polymerizable monomers are used alone or in proper combinations, combinations between di-2-(meth)acryloyloxyethyl-2,2,4-trimethylhexamethylene dicarbamate and triethylene glycol di(meth)acrylate, and 2,2'-bis[4-(3-(meth)acryloyloxy-2-hydroxypropoxy)phenyl]propane and triethylene glycol di(meth)acrylate are preferable.

The amount of the radical polymerizable monomer to be added is 20.0 to 45.0 parts by weight, preferably 20.0 to 40.0 parts by weight, more preferably 20.0 to 35.0 parts by weight based on 100 parts by weight of the whole resin cement formulation. When the amount of the radical polymerizable monomers to be added is less than 20.0 parts by weight, a viscosity of the obtained paste is high and when the amount is more than 45.0 parts by weight, a viscosity of the obtained paste is low and therefore, in both cases, paste properties suitable for using as a resin cement cannot be achieved.

The component (b) fluoroaluminosilicate glass (FASG) filler may be manufactured according to a known glass manufacturing method. For example, a glass composition may be manufactured by melting glass materials selected from silica, alumina, aluminium hydroxide, aluminium silicate, mullite, calcium silicate, strontium silicate, sodium silicate, sodium carbonate, calcium fluoride, aluminium fluoride, strontium fluoride, aluminium phosphate, sodium phosphate and the like at a high temperature of 1000° C. or higher, cooling and pulverizing.

A preferred formulation of the glass composition used in the present invention comprises the following oxides:

| | |
|---|---|
| Calcium oxide (CaO) | 5 to 40 mol %; |
| Silica ($SiO_2$) | 15 to 70 mol %; |
| Alumina ($Al_2O_3$) | 10 to 50 mol %; |
| Sodium oxide ($Na_2O$) | 0 to 7 mol %; |
| Phosphorus pentaoxide ($P_2O_5$) | 0 to 7 mol %; and |
| Fluoride (as F) | 5 to 20 mol %, | provided that a sum of the respective components does not exceed 100 mol %.

In the above glass composition, any alkaline earth metal oxide may be used in place of calcium oxide. In addition, at least a part of the alkaline earth metal may be replaced by a lanthanide metal such as lanthanum, gadolinium, ytterbium and the like.

Further, in the glass composition, a part or all of alumina may be replaced by an oxide of a Group III metal other than aluminium. Similarly, a part of silica in the glass composition may be replaced by zirconium oxide or titanium oxide. In order to invest the glass composition with radiopaque, strontium, lanthanum, gadolinium, ytterbium or zirconium may be used in the glass composition.

The fluorine-containing glass used in the present invention may be manufactured by any conventional method, but preferably by a fusion method or a sol-gel method. The sol-gel method comprises: reacting a first solution containing a soluble aluminium compound and a soluble silicon compound with a second solution containing a soluble compound of a Group II metal, drying the obtained gel by heat drying or freeze drying and collecting. According to this method, use of additives used in conventional glass manufacturing such as flux agents may be avoided and relatively low temperatures may be used. Therefore, glass having higher transparency than conventional ones may be obtained.

Other chemical substances such as an alcohol solution of an organic metal or an inorganic salt may be added to a sol form to obtain divalent or trivalent glass.

An acidic or basic solvent may be added to the sol-gel reaction mixture to enhance a gellation rate. According to this method, homogeneous fire resistant glass is obtained at a relatively low temperature.

The sol-gel method is particularly suitable for manufacturing a glass containing gadolinium and a glass containing the following five components: $X_nO_m$—CaO—$Al_2O_3$—$SiO_2$—F, wherein $X_nO_m$ is an oxide of a radiopaque substance.

Generally, it is difficult to manufacture such a 5-component glass. However, the sol-gel method allows us to manufacture glass easily.

The CaO source may be replaced by aluminium sec-butoxide in isobutyl alcohol and ethanol, the $SiO_2$ source may be replaced by tetraethylsilicate, the F source may be replaced by 40% hydrofluoric acid, the $Gd_2O_3$ source may be replaced by ethanol-soluble $Gd(NO_3)_3$ or a methanol solution thereof.

Further, calcium oxide may be replaced by $Ca(NO_3)_2$ anhydride solved in ethanol at 50° C. These solutions are mixed at 50° C. by stirring. The mixture may be then refluxed at 70° C. After dried, the obtained material is ground while it is soft and then the ground material is dried at a temperature between 400 to 500° C. This is further pulverized into a required size. FASG used in the present invention may be that obtained by the conventional fusion method.

In the present invention, FASG filler having an average particle size of 0.1 to 10 μm, preferably 0.1 to 5 μm may be used. Additionally, the FASG filler is used as filler to enforce cement material itself. In order to improve affinity with resin components such as polymerizable monomers, it is desirable to do silane treatment on the FASG filler by a conventional method. The silane treatment agents include, for example, vinyltrimethoxysilane, vinylethoxysilane, vinyltrichrolosilane, γ-methacryloyloxypropyltrimethoxysilane, γ-mercaptopropyltrimethoxysilane, and γ-aminopropyltriethoxysilane.

The amount of the FASG filler to be added is 50.0 to 80.0 parts by weight, preferably 50.0 to 77.0 parts by weight based on 100 parts by weight of the whole resin cement formulation. When the amount of the FASG filler to be added is less than 50.0 parts by weight, filler sedimentation or so-called a floating liquid phenomenon occurs and when the amount is more than 80.0 parts by weight, fluidity of the paste significantly reduces to deteriorate cement functions.

In addition, for preventing filler sedimentation, ultrafine particle filler may be used as a component (b') additive other than fluoroaluminosilicate used in the present invention.

The component (c)-(1) organic peroxide used in the present invention is not limited, but includes benzoyl peroxide, 4,4'-dichrolobenzoyl peroxide, 2,4-dichrolobenzoyl peroxide, dilauryl peroxide, methyl ethyl keton peroxide, t-butylperoxymaleic acid and succucinic acid and peroxide and the like. Among them, t-butyl peroxymaleic acid succucinic acid peroxide, benzoyl peroxide and 4,4'-dichrolobenzoyl peroxide are particularly preferable.

The component (c)-(2) alkali metal salt or alkaline earth metal salt of barbituric acids used in the present invention is not limited, but includes a sodium salt of 5-n-butylbarbituric acid, a calcium salt of 5-n-butylbarbituric acid, a sodium salt of 1-benzyl-5-phenylbarbituric acid, a calcium salt of 1-benzyl-5-phenylbarbituric acid, a of sodium salt of 1,3,5-trimethylbarbituric acid, a calcium salt of 1,3,5-trimethylbarbituric acid and the like.

The component (c)-(3) photopolymerization initiator used in the present invention is not limited, but includes ultraviolet light sensitizers or visible light sensitizers such as benzoin methyl ether, benzoin ethyl ether, benzoin isopropyl ether, benzoin, benzophenone, thioxanthon, 2-chrolothioxanthon, 2-hydroxy-3-(3,4-dimethyl-9H-thioxanthen-2-yloxy-N,N,N-trimethyl-1-propane aluminium chloride, 9,10-anthraquinone, camphorquinone, benzil, 4,4'-dicyclobenzil, diacetil and the like.

The component (c)-(4) aromatic secondary or tertiary amine used in the present invention is that containing at least one aromatic group on the nitrogen atom, wherein the aromatic group may have a substituent. Specifically, N-dimethylaniline, N-dimethyl-p-toluidine, N,N-di(2-hydroxyethyl)-p-toluidine, N-methyl-p-toluidine and the like are particularly preferable.

The amount of the amine to be used is 0.05 to 0.8 parts by weight, more preferably 0.1 to 0.5 parts by weight based on 100 parts by weight of the whole of the resin cement formulation. When the amount of the amine to be used is less than 0.05 parts by weight, the paste does not cure sufficiently, when the amount of the amine to be used is more than 0.8 parts by weight, the resin cement discolors, and moreover since it cures rapidly, a pot life of the resin cement becomes shorter, a sufficient operating time cannot be secured.

The component (d) shelf life stabilizer used in the present invention includes hydroquinone, hydroquinone monomethyl ether, hydroxymethoxybenzophenone, butylated hydroxytoluene and the like.

The amount of the shelf life stabilizer to be used is 0.02 to 0.2 parts by weight, preferably 0.03 to 0.06 parts by weight based on 100 parts by weight of the whole resin cement formulation. When the amount of the shelf life stabilizer to be used is less than 0.03 parts by weight, the shelf life of the paste becomes insufficient and when the amount is more than 0.2 parts by weight, the paste does not cure sufficiently.

The component (e) water used in the present invention is preferably that is clinically acceptable as a dental care component and is substantially free of impurities harmful to the components in the formulation and to adhesion effects. Distilled water or ion-exchanged water is preferable.

The amount of the water to be added is usually 20.0 to 60.0 weight %, preferably 25 to 50.0 weight %, more preferably 30.0 to 45.0 weight % based on 100 weight % of the whole primer formulation. When the amount of the water to be added is less than 20.0 weight %, adhesion decreases and when the amount is more than 60 weight %, adhesion again decreases.

The component (f) is the polymerizable monomer represented by the general formula (I):

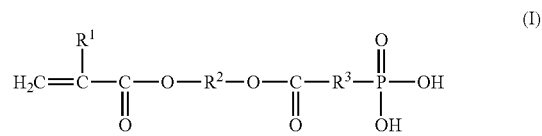

wherein $R^1$ is a hydrogen atom or a methyl group, $R^2$ is an alkylene group having a carbon number of 5 to 10, $R^3$ is an alkylene group having a carbon number of 1 to 6. This polymerizable monomer may be prepared by the method disclosed in Patent Document 7.

The polymerizable monomer represented by the general formula (I) is not limited, but includes the following compounds:

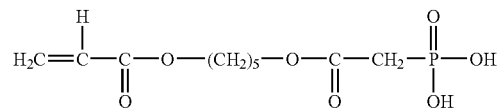

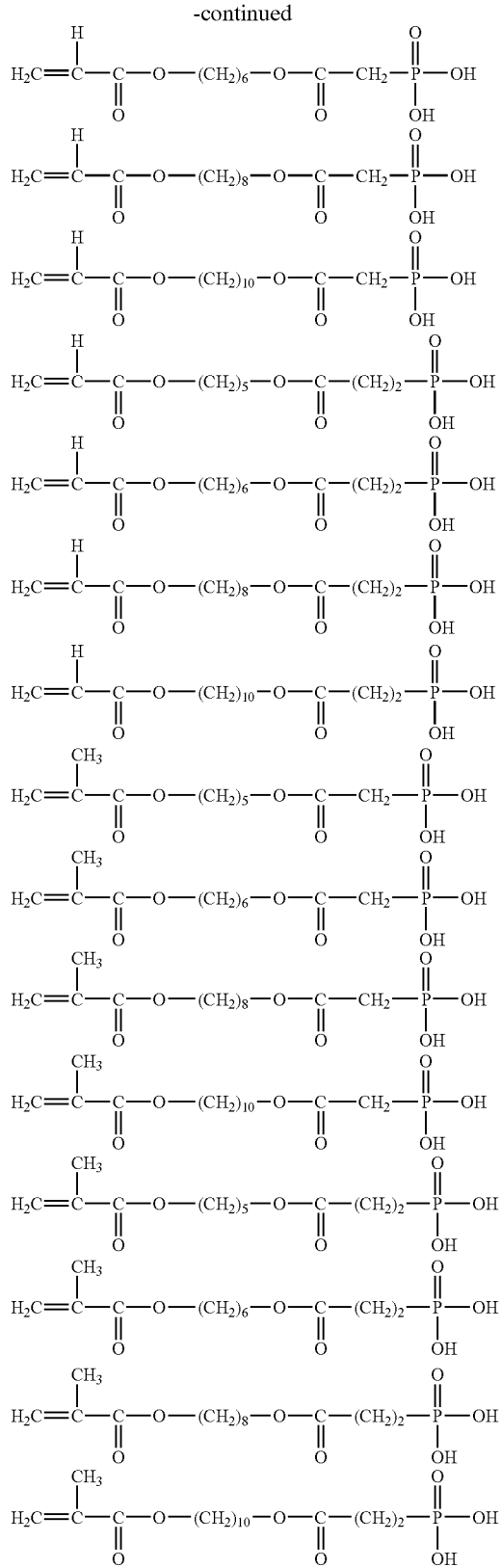

The component (f) polymerizable monomer represented by the general formula (I) used in the present invention has a phosphonate group but never inhibits polymerization and is copolymerized with other radical polymerizable monomers and may be used in radical polymerization curing type dental primers.

The amount of the polymerizable monomer containing a phosphonate group to be added is usually 0.5 to 25.0 weight %, preferably 1.0 to 20.0 weight %, more preferably 2.0 to 10.0 weight %. When the amount is less than 0.5 weight % or more than 25.0 weight %, adhesion decreases.

The component (g) polymerizable monomer containing a dibasic acid carboxyl group and polymerizable monomers containing acid anhydride is not limited, but includes 1,4-di(meth)acryloxyethylpyromellitric acid, 4-(meth)acryloxybutyltrimellitric acid, 4-(meth)acryloxyhexyltrimellitric acid, 4-(meth)acryloxydecyltrimellitric acid, 4-acryloxybutyltrimellitric acid, 11-(meth)acryloxy-1,1-undecanedicarboxylic acid and the like. Particularly preferable are 4-(meth)acryloxyethyltrimellitric acid and 4-(meth)acryloxyethyltrimellitric acid anhydride. In this text, the term "(meth)acryloxy" means acryloxy or methacryloxy.

The amount of the polymerizable monomers containing a dibasic acid carboxyl group and polymerizable monomers containing acid anhydride to be added is usually 2.0 to 40.0 weight %, preferably 5.0 to 35.0 weight %, more preferably 5.0 to 25.0 weight % based on 100 weight % of the whole primer formulation. When the amount of the polymerizable monomer to be added is less than 2.0 weight % or more than 25.0 weight %, adhesion decreases and, when the amount is more than 40.0 weight %, solubility decreases.

The component (h) barbituric acid used in the present invention is not limited but includes a barbituric acid derivative represented by the following formula:

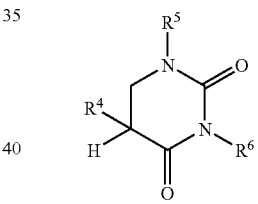

wherein $R^4$, $R^5$ and $R^6$ are the same or different and independently each other represent a hydrogen atom or an aliphatic group, an aromatic group, an alicyclic group or a heterocyclic group, each of which may have substituents such as a halogen atom, an alkyl group, an alkoxy group, an aryl group, a cyclohexyl group and the like.

These barbituric acids include, for example, barbituric acid, 1,3-dimethylbarbituric acid, 1-methylbarbituric acid, 1,3-diphenylbarbituric acid, 5-butylbarbituric acid, 1,5-dimethylbarbituric acid, 5-ethylbarbituric acid, 5-isopropylbarbituric acid, 5-cyclohexylbarbituric acid, 1,3,5-trimethylbarubituric acid, 1,3-dimethyl-5-ethylbarbituric acid, 1,3-dimethyl-5-n-butylbarbituric acid, 1,3-dimethyl-5-secbutylbarbituric acid, 1,3-dimethyl-5-isobutylbarbituric acid, 1,3-dimethyl-5-tert-butylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-benzyl-5-phenylbarbituric acid, 1-cyclohexyl-5-ethylbarbituric acid, 5-aminobarbituric acid, and 2-chrolobarbituric acid and the like. Particularly preferable are 5-butylbarbituric acid, 1,3,5-trimethylbarbituric acid, 1,3-dimethyl-5-isobutylbarbituric acid, 1-benzyl-5-phenylbarbituric acid and 1-cyclohexyl-5-ethylbarbituric acid.

The amount of the barbituric acids to be added is usually 1.0 to 5.0 weight %, preferably 0.8 to 4.0 weight %, more preferably 1.0 to 3.0 weight % based on 100 weight % of the whole primer formulation. When the amount of the barbituric acids to be added is less than 1.0 weight %, adhesion decreases and when the amount is more than 5.0 weight %, adhesion decreases again and, since a pot life of the resin cement becomes shorter, a sufficient operating time cannot be secured.

The component (i) amine used in the present invention is not limited but includes the compound represented by the general formula:

wherein $R^7$, $R^8$ and $R^9$ are the same or different and independently each other represent a hydrogen atom; an alkyl group having a carbon number of 1 to 10 or a cycloalkyl group having a carbon number of 6 to 12, each of which may have a substituent such as a hydroxy group or a (meth)acryloyl group and the like; or a phenyl group which may have a substituent such as halogen, an alkyl group having a carbon number of 1 to 10, a hydroxy group, a (meth)acryloyl group and the like, provided that $R^1$ to $R^3$ are not hydrogen atoms at the same time.

In addition, cyclic amines or di- or higher valent amines, for example, diamines are included. This type of amine includes n-butylamine, propylamine, pentylamine, hexylamine, dimethylamine, diethylamine, dipropylamine, di-n-butylamine, dipentylamine, trimethylamine, triethylamine, tripropylamine, tri-n-butylamine, tripentylamine, trihexylamine, phenylethylamine, ethyleneamine, tetramethyleneamine, N,N-dimethylaminoethyl methacrylate, N,N-diethylaminoethyl methacrylate, monoethanolamine, N-methyldiethanolamine, triethanolamine, aniline, methylaniline, dimethylaniline, diphenylamine, triidine, anisidine, N,N-dimethyl-m-anisidine, N,N-dimethyl-p-anisidine, N,N-dimethyl-m-aminophenol, N,N-diethyl-m-aminophenol, N,N-diethyl-p-anisidine, p-propoxy-N,N-dimethylaniline, p-hexyloxy-N,N-dimethylaniline, p-butoxy-N,N-dimethylaniline, chroloaniline, bromoaniline, dimethyl-p-toluidine, N,N-di(2-hydroxyethyl)-p-toluidine, p-aminophenyl methacrylate, N,N-dimethylaminophenyl methacrylate, N,N-di(2-hydroxyethyl)phenyl methacrylate, p-(2-hydroxy-3-methacryloxypropoxy)phenylamine, N,N-di(2-hydroxyethyl)phenyl-glycidyl (meth)acrylate, N-methylmorpholine, imidazole, 1-methylimidazole, 2-methylimidazole, 2-methyl-4-methylimidazole, ethylenediamine, methylenedianiline, phenylenediamine, N,N-bis(hydroxyethyl)diethylene triamine, N,N-bis(hydroxyethyl) diethylenetriamine, N,N-bis(hydroxyethyl)triethylene tetramine, 3-amino-1,2-propanediol, DL-1-amino-2-propanol, 2-amino-4-phenylphenol, 2-amino-2-phenylethanol, L-2-amino-1-propanol, 3-amino-1-propanol, 2-anilino-ethanol, N,N-dihydroxyethylaniline, o- or p-aminophenetylalcohol, 5-amino-1-pentanol, 5-amino-2-methylphenol, 2-amino-5-methylphenol, aminobenzoate, for example, methyl p-aminobenzoate, ethyl p-aminobenzoate, butyl p-aminobenzoate, propyl p-aminobenzoate, isopropyl p-aminobenzoate, ethyl 4-dimethylaminobenzoate, isopropyl 4-dimethylaminobenzoate and the like. N,N-di(2-hydroxyethyl)-p-toluidine, N,N-dimethylaminoethyl methacrylate, p-aminophenyl methacrylate, p-(β-hydroxy-γ-methacryloxypropoxy)phenylamine, triethanolamine, monoethanolamine, isopropyl 4-dimethylaminobenzoate, ethyl 4-dimethylaminobenzaote and the like are preferable, N,N-di(2-hydroxyethyl)-p-toluidine or dimethy L-p-toluidine are particularly preferable.

The amount of the amines to be added is usually 0.01 to 10.0 weight %, preferably 1.0 to 5.0 weight %, more preferably 0.8 to 4.0 weight % based on 100 weight % of the whole primer formulation. When the amount of the amines to be added is less than 1.0 weight %, adhesion decreases and when the amount is more than 5.0 weight %, adhesion decreases again and, since a pot life of the resin cement becomes shorter, a sufficient operating time cannot be secured.

The dental resin cement and the dental primer according to the present invention may optionally contain a polymerizable compound containing a hydroxide group as a component (j). The polymerizable compound containing a hydroxide group includes polymerizable monomers, oligomers or polymers containing a hydroxide group and a polymerizable unsaturated group such as an acryloyl group, a methacryloyl group, a vinyl group or an allyl group and the like. Monomers are particularly preferable. These compounds include 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono (meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di (meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth)acrylate and 2,3-dihydroxypropyl (meth)acrylate are particularly preferable. Optionally, these compounds containing a hydroxide group may be used by appropriately mixing two or more of them.

The amount of the compound containing a hydroxide group to be added is usually 2.0 to 20.0 weight %, preferably 5.0 to 15.0 weight % based on 100 weight % of the whole primer formulation. When the amount of the compound containing a hydroxide group to be added is less than 2.0 weight % or more than 20.0 weight %, adhesion decreases.

The primer composition of the present invention may optionally contain water miscible organic solvents as a component (k). The water miscible organic solvents are added to enhance solubility of the component (g) polymerizable monomers containing a dibasic acid carboxyl group and the polymerizable monomers containing acid anhydride and the like, to form a homogeneous solution and to improve adhesion. The water miscible organic solvents are not limited, but include alcohol compounds such as methyl alcohol, ethyl alcohol, 1-propanol, isopropyl alcohol, 2-methyl-1-propanol, 2-methyl-2-butanol, 2-propen-1-ol, 1,3-butanediol, 1,4-butanediol, 1,2,6-hexanetriol, trimethylolpropane, diethylene glycol, triethylene glycol, tetraethylene glycol, propylene glycol, 2-methoxyethanol, 2-ethoxyethanol, 2-(methoxy) ethoxyethanol, 2-ethoxymethoxyethanol and the like; or keton compounds such as acetone, methyl ethyl keton and the like. Among them, ethyl alcohol, isopropyl alcohol and acetone are preferable. These water miscible organic solvents may be used by mixing two or more of them, if needed.

The amount of the water miscible organic solvent to be added is usually 0.0 to 50.0 weight %, preferably 0.0 to 35.0 weight %, more preferably 0.0 to 30.0 weight % based on 100 weight % of the whole primer formulation. When the amount of the water miscible organic solvent to be added is more than 50.0 weight %, the viscosity of the paste becomes significantly decreases and then it is difficult to obtain a proper amount from a package.

Each of the composite resin cement and the primer according to the present invention is used in a divided package form in which the components are divided into two or more packages, if needed. For example, a combination of an organic peroxide and an aromatic tertiary amine and a combination of an amine and a polymerizable monomer containing an acidic group are unfavorable because the components in these combinations react each other. Therefore, it is desired that components are combine not to react each other in a paste or a primer liquid.

For example, when hardening agent components comprises an initiator and a promoter and the like, they are divided into two or more packages so as to mix prior to use. Mixing methods regarding a primer are properly selected from a method for mixing components in a container such as a small dish, in a cavity of a patient's tooth to be restored and the like prior to use by a dentist. The divided forms may be appropriately selected from their combinations.

EFFECTS OF THE INVENTION

The dental adhesive kit of the present invention enables excellent adhesion to dentin, which is difficult for conventional adhesives, because the adhesive has high adhesion and the primer particularly is rich in hydrophilicity.

Further, although the dental composite resin cement is in a two-paste type, it is excellent in storage stability.

BEST MODE FOR CARRYING OUT THE INVENTION

Below the present invention will be explained in detail, but the present invention never limited in these Examples.

Abbreviations and acronyms used in the Examples are as follows:

(1) Polymerizable Monomers

[Polymerizable Monomers Represented by the General Formula (I)]
  2-MEPA: (2-methacryloxy)ethylphosphonoacetate
  2-MEPP (2-methacryloxy)ethyl-3-phosphonopropionate
  6-MHPA (6-methacryloxy)hexylphosphonoacetate
  6-MHPP: (6-methacryloxy)hexyl-3-phosphonopropionate
  10-MDPA: (10-methacryloxy)decylphosphonoacetate
  10-MDPP: (10-methacryloxy)decyl-3-phosphonopropionate

[Polymerizable Monomers Containing a Dibasic Carboxyl Group or Acid Anhydride]
  4-AET: 4-acryloxyethyltrimellitric acid
  4-META: 4-methacryloxyethyltrimellitric acid anhydride

[Other Polymerizable Monomers]
  UDMA: di-2-methacryloyloxyethyl-2,2,4-trimethylhexamethylenedicarbamate
  3G: triethylene glycol dimethacrylate
  Bis-GMA: 2,2'-bis[4-(3-(meth)acryloyloxy-2-hydroxypropoxy)phenyl]propane (2) Polymerizing Catalysts

[Barbituric Acids]
  BBA: 5-n-butylbarbituric acid
  BPBA: 1-benzyl-5-phenylbarbituric acid
  TMBA: 1,3,5-trimethylbarbituric acid

[Salts of Barbituric Acids]
  BBA.Na: sodium 5-n-butylbarbiturate
  BBA.Ca: calcium 5-n-butylbarbiturate
  BPBA.Na: sodium 1-benzyl-5-phenylbarbiturate
  BPBA.Ca: calcium 1-benzyl-5-phenylbarbiturate
  TMBA.Na: sodium 1,3,5-trimethylbarbiturate
  TMBA.Ca: calcium 1,3,5-trimethylbarbiturate

[Amines]
  DEPT: N,N-di(2-hydroxyethyl)-p-toluidine

[Other Polymerizing Catalysts]
  p-TSNa: sodium p-toluenesulphinate (3) Filler

[Glass Filler]
  FASG filler: fluoroaluminosilicate glass filler
  Average particle size 1.8 μm, γ-methacryloyloxypropyltrimethoxysilane 8% silane treated filler

[Other Filler]
  R-711: Ultrafine particle silica filler
  R-972: Ultrafine particle silica filler
  R-974: Ultrafine particle silica filler

EXAMPLES

Measurement methods for properties of resin cements and primers used in the Examples are shown below.

(1) Measurements in TG (Thermogravimetric Analysis)/DTA (Differential Thermal Analysis)

A sample to be analyzed was placed into an aluminium sample container (an aluminium pan) and it was then mounted on a Thermogravimetric/Differential Thermal Analyzer (manufactured by Seiko Instrument Inc.). Measurements were carried out at a heating rate of 10° C./min. with introducing a nitrogen gas at 200 mL/min. with respect to alumina as a reference.

(2) Measurement for pH

A two weight % aqueous solution was prepared and then pH of the solution was measured five minutes after dipping electrodes by using a pH meter F-22 (manufactured by Horiba Ltd.) calibrated at two points.

(3) Paste Storage Stability

Into a pen type container Syringe US-18C (manufactured by Unicosmo Corporation) was filled about 4.5 g of a paste to be evaluated. This pen type container has a mechanism that a predetermined amount of the content is extruded by rotating a rear part of the pen to promote a piston. Due to this mechanism, an area of the interface between the content and the air may be minimized.

The pen type container filled with the paste was stored in an incubator MIR-153 (manufactured by Mitsubishi Electric Corporation) and gellation was monitored every 24 hours. If the existence of solids is confirmed by visual observations after extruding a predetermined amount of the paste from the container and smearing it with a spatula, then it is determined that paste gellation occurs.

(4) Measurement for Curing Time of Resin cement

A curing time of a mixture of a paste A and a paste B was measured according to ISO 4049:2000(E).

Specifically, 0.8 g of a paste mixture was filled into a sample well (4 mm$\phi$×6 mm) provided with a thermo couple and exothermal curve by curing reaction was recorded. The curing time is defined to be a time period from a start time of mixing to a time at a peak in the exothermal curve. The average value is calculated from three measurements.

(5) Measurement of Adhesion Strength

Adhesion strength is defined as tensile strength between enamel or dentin and a stainless rod having a diameter of 4.55 mm with resin cement intervening at the interface.

Fresh extracted bovine anterior teeth were used as tooth substances in place of human teeth. Their tooth roots were removed and then they were buried in epoxy resin. In an adhesion test, a lip side of the same bovine tooth was abraded with water resistant abrasion paper (SiC #600) to expose enamel or dentin. After water washing and air drying the exposed surface, the surface was treated by applying a mixture of dental adhesive primer liquids I and II on the surface and by air drying after 20 seconds.

On the other hand, the stainless rod was used after previously abrading the surface to be adhered with water resistant abrasion paper (SiC #600), sand blasting with alumina powder having a particle size of about 50 μm, applying a metal primer Metal Link (manufactured by Shofu Inc.) and by natural drying for 10 seconds.

Equivalent amounts of the paste A and the paste B of the resin cement were taken out on a paper mixing plate and they were mixed for 15 seconds with a plastic spatula. The tooth substance and stainless rod were adhered by applying a 200 g load with the mixed pasts intervening.

Excess pastes were removed with a microbrush and then a light was irradiated along a cement line for 10 seconds using a light irradiator Grip Light II (manufactured by Shofu Inc.). The load was removed 10 minutes after light irradiation. After immersing the adhesion specimen into distilled water at 37±2° C. for 24 hours with considering the oral circumstances, a tensile strength was measured using an Instron Universal tester (Instron 5567, manufactured by Instron Corp.) at a crosshead speed of 1 mm/min.

After immersing the same specimen into distilled water at 37±2° C. for 24 hours, and carrying out 2000 cycles of immersion into 4° C. water for 1 minute and immersion into 60° C. water for 1 minute, an adhesion strength after the aging test was measured.

(6) Measurement of Workable Time

In order to clarify a pot life of a resin cement, a workable time was introduced as a parameter for workability of the resin cement. The workable time is defined as a time period until the resin cement becomes irremovable by a hand press on a primer treated surface in a clinical simulation test.

In the present invention, a clinical latitude for the workable time is set to 20 to 60 seconds.

Tooth Specimens:

Fresh extracted bovine anterior teeth were used as tooth substances in place of human teeth. Their tooth roots were removed and then they were buried in epoxy resin. The specimen was ground to expose enamel and the surface was abraded with water resistant abrasion paper (SiC #600) followed by water washing and drying the exposed surface to prepare a tooth specimen.

Primer Treatment:

Equivalent amounts of a primer liquid I and a primer liquid II were taken out and they were mixed with a small brush and the like. Then, the surface of the specimen was treated by applying a mixture for 20 seconds followed by air drying.

Metal Adherend:

A stainless rod (SUS303) having a diameter of 4.55 mm was used as a metal adherend. A surface of the stainless rod to be adhered was treated by sand blasting for 10 seconds with alumina powder having a particle size of about 50 μm using ca. 0.5 MPa compressed air. After water washing and drying, a metal adhesion promoting primer Metal Link (manufactured by Shofu Inc.) was applied followed by natural drying for 10 seconds.

Adhering:

Mixed resin cement was applied between the tooth sample treated with the primer and the metal adherend treated with Metal Link to bind them.

Measurement of Workable Time:

The bound sample was mounted on a dry type thermostatic chamber set at 37±2° C. with considering the oral circumstances, it was monitored whether the stainless rod was movable by hand press every 5 seconds, and a time period until the rod became irremovable to obtain the workable time. The average value was calculated from measurements for three samples.

(7) Measurement of Flexural Strength

Flexural strength ($\sigma$, MPa) was calculated from the following equation according to ISO 4049:2000(E).

$$\sigma = 3F \cdot I/2bh^2$$

wherein
F: a maximum load applied to a sample (N)
I: a distance between supporting rods (mm)
b: a width of a sample just before testing (mm)
h: a height of a sample just before testing (mm)

Specifically, the resin cement mixture was filled in a stainless mold on a slide glass and another side glass was pressed to the stainless mold. A cured material was obtained by irradiating a light on one side for 20 seconds, 5 times and on the other side for 20 seconds, 5 times with attaching a muzzle of a light irradiator Grip Light II (manufactured by Shofu Inc.) to the slide glasses. The whole areas on the both sides were irradiated by moving the light irradiator.

Molding flash was removed by gently abrading with #320 abrasion paper to obtain a 2×2×25 mm rectangular bar. After immersing this bar into water at 37±2° C. for 24 hours with considering the oral circumstances, a three-point flexural strength was measured using an Instron Universal tester (Instron 5567, manufactured by Instron Corp.) at a distance between the supports of 20 mm and at a crosshead speed of 1 mm/min., an average value of measurements for 5 samples.

Preparation Example 1

Preparation of sodium 5-n-butylbarbiturate

Into a 100 mL conical flask was placed 25 g of distilled water, and sodium carbonate anhydride 3.11 g (29.34 mmol) was added to this while stirring, and was solved in a 30° C. water bath to obtain a $Na_2CO_3$ aqueous solution.

Separately, into a 200 mL conical flask was placed 20 g of distilled water, and 5-n-butylbarbituric acid (BBA) 10.82 g (58.74 mmol) was added to this while stirring, and was uniformly dispersed to obtain a BBA suspension.

The $Na_2CO_3$ aqueous solution was gently poured into the BBA suspension and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted BBA, the obtained white crystals were extensively washed with acetone and the remained crystals were vacuum dried to obtain a sodium salt of 5-n-butylbarbituric acid (BBA.Na).

According to a thermogravimetric analysis (TG) and a differential thermal analysis (DTA), a melting point and a decomposition temperature of the obtained salt were measured and a pH of a 2 weight % aqueous solution of the obtained salt was measured. Based on these results, it was confirmed that a pure barbiturate was formed. The results are shown in Table 1.

Preparation Example 2

Preparation of calcium 5-n-butylbarbiturate

Into a 100 mL conical flask was placed 25 g of distilled water, and calcium carbonate anhydride 5.88 g (58.75 mmol) was added to this while stirring, and was solved in a 30° C. water bath to obtain a $CaCO_3$ suspension.

Separately, into a 200 mL conical flask was placed 20 g of distilled water, and 5-n-butylbarbituric acid (BBA) 10.82 g (58.74 mmol) was added to this while stirring, and was uniformly dispersed to obtain a BBA suspension.

The $CaCO_3$ suspension was gently poured into the BBA suspension and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted BBA, the obtained white crystals were extensively washed with acetone and the remained crystals were vacuum dried to obtain a calcium salt of 5-n-butylbarbituric acid (BBA.Ca).

According to a thermogravimetric analysis (TG) and a differential thermal analysis (DTA), a melting point and a decomposition temperature of the obtained salt were measured and a pH of a 2 weight % aqueous solution of the obtained salt was measured. Based on these results, it was confirmed that a pure barbiturate was formed. The results are shown in Table 1.

Preparation Example 3

Preparation of sodium 1-benzyl-5-phenylbarbiturate

Into a 100 mL conical flask was placed 25 g of distilled water, and sodium carbonate anhydride 3.11 g (29.34 mmol) was added to this while stirring, and was solved in a 30° C. water bath to obtain a $Na_2CO_3$ aqueous solution.

Separately, into a 200 mL conical flask was placed 40 g of distilled water and 6 g of acetone, and 1-benzyl-5-phenylbarbituric acid (BPBA) 17.29 g (58.75 mmol) was added to this while stirring to obtain a BPBA acetone/aqueous solution.

The $Na_2CO_3$ aqueous solution was gently poured into the BPBA acetone/aqueous solution and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted BPBA, the obtained white crystals were extensively washed with acetone and the remained crystals were vacuum dried to obtain a sodium salt of 1-benzyl-5-phenyl barbituric acid (BPBA.Na).

According to a thermogravitmetric analysis (TG) and a differential thermal analysis (DTA), a melting point and a decomposition temperature of the obtained salt were measured and a pH of a 2 weight % aqueous solution of the obtained salt was measured. Based on these results, it was confirmed that a pure barbiturate was formed. The results are shown in Table 1.

Preparation Example 4

Preparation of calcium 1-benzyl-5-phenylbarbiturate

Into a 100 mL conical flask was placed 25 g of distilled water, and calcium carbonate anhydride 5.88 g (58.75 mmol) was added to this while stirring, and was solved in a 30° C. water bath to obtain a $CaCO_3$ suspension.

Separately, into a 200 mL conical flask was placed 40 g of distilled water and 6 g of acetone, and 1-benzyl-5-phenylbarbituric acid (BPBA) 17.29 g (58.75 mmol) was added to this while stirring to obtain a BPBA acetone/aqueous solution.

The $CaCO_3$ suspension was gently poured into the BPBA acetone/aqueous solution and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted BPBA, the obtained white crystals were extensively washed with acetone and the remained crystals were vacuum dried to obtain a calcium salt of 1-benzyl-5-phenyl barbituric acid (BPBA.Ca).

Preparation Example 5

Preparation of sodium 1,3,5-trimethylbarbiturate

Into a 100 mL conical flask was placed 25 g of distilled water, and sodium carbonate anhydride 3.11 g (29.34 mmol) was added to this while stirring, and was solved in a 30° C. water bath to obtain a $Na_2CO_3$ aqueous solution.

Separately, into a 200 mL conical flask was placed 20 g of distilled water, and 1,3,5-trimethylbarbituric acid (TMBA) 10.00 g (58.76 mmol) was added to this while stirring, and was uniformly dispersed to obtain a TMBA suspension.

The $Na_2CO_3$ aqueous solution was gently poured into the TMBA suspension and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted TMBA, the obtained white crystals were extensively washed with acetone and the remained crystals were vacuum dried to obtain a sodium salt of 1,3,5-trimethylbarbituric acid (TMBA.Na).

According to a thermogravimetric analysis (TG) and a differential thermal analysis (DTA), a melting point and a decomposition temperature of the obtained salt were measured and a pH of a 2 weight % aqueous solution of the obtained salt was measured. Based on these results, it was confirmed that a pure barbiturate was formed. The results are shown in Table 1.

Preparation Example 6

Preparation of calcium 1,3,5-trimethylbarbiturate

Into a 100 mL conical flask was placed 25 g of distilled water, and calcium carbonate anhydride 5.88 g (58.75 mmol) was added to this while stirring, and was solved in a 30° C. water bath to obtain a $CaCO_3$ suspension.

Separately, into a 200 mL conical flask was placed 20 g of distilled water, and 1,3,5-trimethylbarbituric acid (TMBA) 10.00 g (58.76 mmol) was added to this while stirring, and was uniformly dispersed to obtain a TMBA suspension.

The $CaCO_3$ suspension was gently poured into the TMBA suspension and the mixture was reacted by stirring in a 30° C. water bath for 1 hour. Then, the reaction mixture was evaporated to about 40 g at 70 cmHg in a 40 to 50° C. water bath. To the residue was added ca. 200 mL acetone to crystallize and then solid-liquid separation was carried out. In order to remove unreacted TMBA, the obtained white crystals were extensively washed with acetone and the remained crystals were vacuum dried to obtain a calcium salt of 1,3,5-trimethylbarbituric acid (TMBA.Ca).

According to a thermogravimetric analysis (TG) and a differential thermal analysis (DTA), a melting point and a decomposition temperature of the obtained salt were measured and a pH of a 2 weight % aqueous solution of the obtained salt was measured. Based on these results, it was confirmed that a pure barbiturate was formed. The results are shown in Table 1.

TABLE 1

Melting Point, Decomposition Temperature and pH for the barbituric acid compounds

|  |  | m.p. (° C.) | decomp. temp. (° C.) | pH |
|---|---|---|---|---|
| Prep. Ex. 1 | BBA•Na | — | 377.6 | 7.2 |
| Prep. Ex. 2 | BBA•Ca | — | 410.4 | 7.6 |
|  | BBA | 152.3 | 239.8 | — |
| Prep. Ex. 3 | BPBA•Na | — | 368.4 | 7.3 |
| Prep. Ex. 4 | BPBA•Ca | — | 346.0 | 7.4 |
|  | BPBA | 155.0 | 232.3 | — |
| Prep. Ex. 5 | TMBA•Na | — | 497.1 | 7.8 |
| Prep. Ex. 6 | TMBA•Ca | — | 588.2 | 7.5 |
|  | TMBA | 74.6 | 176.3 | — |

Example 1

Effects of Barbituric Acid Compounds on Storage Stability of Resin Cement (1) Manufacture of Resin Cement Based on a formulation shown in Table 2, two-paste type resin cements consisting of a paste A and a paste B were manufactured.

In this Example, a sum of the components other than the component (c)-(2) in the paste A was set to 50 parts by weight and 0.001 moles of a barbituric acid compound was added in the paste A. The sum of the components of the paste B was set to 50 parts by weight.

Resin cements 1 to 6 were manufactured by using each of the barbituric acid salts prepared in Preparation Examples 1 to 6 in Table 3 as barbituric acid compounds shown in Table 2. For comparison, Resin cements 7 to 9 were manufactured by using each of barbituric acids corresponding to the barbituric acid salts prepared in Preparation Examples 1 to 6 in Table 3 as barbituric acid compounds shown in Table 2. Additionally, the formulation of the paste B was common for the resin cements.

TABLE 2

Formulation of Resin Cement

| Paste |  | Ingredients | Contents (parts by weight) |
|---|---|---|---|
| A | (a) | Bis-GMA | 9.60 |
|  |  | 3G | 6.40 |
|  | (b) | FASG filler | 32.33 |
|  | (b') | R-711 | 1.50 |
|  | (c)-(2) | Barbituric acid compound*[1] | 0.001 moles |
|  | (c)-(4) | DEPT | 0.15 |
|  | (d) | BHT | 0.02 |
| B | (a) | UDMA | 9.60 |
|  |  | 3G | 5.30 |
|  | (b) | FASG filler | 33.38 |
|  | (b') | R-711 | 1.50 |
|  | (c)-(1) | BPO | 0.10 |
|  | (c)-(3) | CQ | 0.10 |
|  | (d) | BHT | 0.02 |

*[1]The salts of barbituric acids according to Manufacturing Examples 1 to 6 and corresponding barbituric acids are included.

TABLE 3

Barbituric acid compound in Paste A

| Resin Cement |  | Barbituric acid compound |
|---|---|---|
| 1 | Prep. Ex. 1 | BBA•Na |
| 2 | Prep. Ex. 2 | BBA•Ca |
| 7 |  | BBA |
| 3 | Prep. Ex. 3 | BPBA•Na |
| 4 | Prep. Ex. 4 | BPBA•Ca |
| 8 |  | BPBA |
| 5 | Prep. Ex. 5 | TMBA•Na |
| 6 | Manuf. Ex. 6 | TMBA•Ca |
| 9 |  | TMBA |

(2) Characterization of Resin Cement

[Storage Stability of Paste A]

Results from measuring storage stability for each of the pastes A at 30° C. and 50° C. are listed in Table 4.

TABLE 4

Storage stability of Paste A

|  |  | Gellation time | |
|---|---|---|---|
| Resin Cement | Barbituric acid compound | 30° C. | 50° C. |
| 1 | BBA•Na | over 20 days | 9 days |
| 2 | BBA•Ca | over 20 days | 12 days |
| 7 | BBA | 6 days | 2 days |
| 3 | BPBA•Na | over 20 days | 12 days |
| 4 | BPBA•Ca | over 20 days | 12 days |
| 8 | BPBA | 2 days | 1 day |
| 5 | TMBA•Na | over 20 days | 11 days |
| 6 | TMBA•Ca | over 20 days | 24 days |
| 9 | TMBA | 5 days | 2 days |

When the storage temperature was 30° C., the respective pastes A for resin cements 7 to 9 using barbituric acid showed a gellation time of 2 to 6 days, while the respective pastes A for the resin cements 1 to 6 using a salt of barbituric acid showed a gellation time of 9 to 24 days.

By using a salt of barbituric acid in place of barbituric acid, the storage stability of Paste A was significantly improved.

[Curing Time for Resin Cement]

For respective resin cements, curing times which is a time period from mixing of the paste A and the paste B to cure were measured in an initial stage immediately after paste manufacture and 30 days and 90 days after storing at 23±1° C. or 30±1° C. with considering usual storage conditions. Results of measuring curing times are listed in Table 5.

TABLE 5

Curing Time for Resin Cement (seconds)

| Resin Cement | Initial | 23° C. after 30 days | 23° C. after 90 days | 30° C. after 30 days | 30° C. after 90 days |
|---|---|---|---|---|---|
| 1 | 225 | 195 | 234 | 218 | 269 |
| 2 | 252 | 250 | 235 | 195 | 272 |
| 7 | 192 | 195 | 324 | gel | — |
| 3 | 274 | 212 | 286 | 228 | 312 |
| 4 | 225 | 231 | 294 | 238 | 318 |
| 8 | 318 | 323 | 438 | gel | — |
| 5 | 190 | 195 | 333 | 286 | 388 |
| 6 | 415 | 428 | 489 | 431 | 569 |
| 9 | 318 | 205 | 362 | gel | — |

The curing times for the resin cements 1 to 6 using a salt of barbituric acid in the paste A were almost constant from the initial stage to 90 days after storage at 23±1° C. or 30±1° C. On the other hand, the curing times for the resin cements 7 to 9 using barbituric acid in the paste A did not greatly changed until 90 days after storage at 23° C. However, when stored at 30° C., gellation occurred after 30 days and, therefore, measurement of curing time was impossible.

By using a salt of barbituric acid in place of bartituric acid, the storage stability of resin cement was significantly improved.

Example 2

Effects of Primer Formulation on Resin Cement Properties (1)

(1) Manufacture of Resin Cement

Based on a formulation shown in Table 6, a two-paste type resin cement 10 consisting of a paste A and a paste B was manufactured.

In this Example, a sum of the components other than the component (d) shelf life stabilizer in the paste A or the paste B was set to 50 parts by weight with respect to the whole resin cement formulation, respectively, and an appropriate amount of a shelf life stabilizer was added in each pastes.

TABLE 6

Formulation of Resin Cement 10

| Paste | | Ingredient | Content (parts by weight) |
|---|---|---|---|
| A | (a) | Bis-GMA | 10.0 |
|   |     | 3G | 5.0 |
|   | (b) | FASG filler | 33.1 |
|   | (b') | R-972 | 1.5 |
|   | (c)-(2) | BBA•Na | 0.2 |
|   | (c)-(4) | DEPT | 0.2 |
|   | (d) | BHT | 0.01 |
| B | (a) | UDMA | 10.0 |
|   |     | 3G | 5.0 |
|   | (b) | FASG filler | 33.3 |
|   | (b') | R-711 | 1.5 |

TABLE 6-continued

Formulation of Resin Cement 10

| Paste | | Ingredient | Content (parts by weight) |
|---|---|---|---|
| | (c)-(1) | BPO | 0.1 |
| | (c)-(3) | CQ | 0.1 |
| | (d) | BHT | 0.03 |

(2) Manufacture of Primer

Based on a formulation shown in Table 7, primers 1 to 8 consisting of a liquid I and a liquid II were manufactured.

In this Example, a sum of the components in the liquid I or the liquid II was set to 50 parts by weight with respect to the whole primer formulation, respectively. Additionally, the formulation of the liquid II was common for the primers.

TABLE 7

Formulation of Primers

| | | Ingredient | Primer 1 | 2 | 3 | 4 | 5 | 6 | 7 | 8 |
|---|---|---|---|---|---|---|---|---|---|---|
| Liquid I (wt. %) | (e) | Distilled water | 37 | 42 | 40 | 37 | 39 | 40 | 32 | 22 |
|  | (h) | TMBA | 2 | — | 2 | — | — | 1 | 5 | 10 |
|  |  | p-TSNa | — | — | — | 2 | — | — | — | — |
|  | (i) | DEPT | 3 | — | — | 3 | 3 | 1 | 5 | 10 |
|  | (x) | Acetone | 8 | 8 | 8 | 8 | 8 | 8 | 8 | 8 |
| Liquid II (wt. %) | (f) | 6-MHPA | 8 | 8 | 8 | 8 | 8 | 8 | 8 | 8 |
|  | (g) | 4-AET | 15 | 15 | 15 | 15 | 15 | 15 | 15 | 15 |
|  | (j) | 2-HEMA | 20 | 20 | 20 | 20 | 20 | 20 | 20 | 20 |
|  | (k) | Acetone | 7 | 7 | 7 | 7 | 7 | 7 | 7 | 7 |

(3) Evaluation of Resin Cement Properties

[Adhesion Strength]

Tooth specimens (enamel and dentin) surface-treated with the primers 1 to 8 were used to measure adhesion strength of the resin cement 10 of the present invention. For comparison, tooth specimens (enamel and dentin) without surface-treatment were used to measure adhesion strength of the resin cement 10 of the present invention similarly. Results from measuring are listed in Table 8.

[Workable Time]

Tooth specimens (enamel and dentin) surface-treated with the primers 1 to 8 were used to measure workable time of the resin cement 10 of the present invention. For comparison, tooth specimens (enamel and dentin) without surface-treatment were used to measure workable time of the resin cement 10 of the present invention similarly. Results from measuring are listed in Table 8.

TABLE 8

Evaluation of Properties for Resin Cement

| | | Primer | | | | | | | | |
|---|---|---|---|---|---|---|---|---|---|---|
| Evaluated property | | None | 1 | 2 | 3 | 4 | 5 | 6 | 7 | 8 |
| Avg. (SD) of Adhesion Strength (MPa) | Enamel | 7.09 (2.43) | 14.08 (4.39) | 11.08 (4.96) | 15.11 (5.84) | 11.20 (3.91) | 9.45 (2.66) | 18.24 (3.67) | 12.52 (2.46) | 7.98 (2.20) |
| | Dentin | 0.51 (0.32) | 8.11 (2.15) | 1.89 (0.63) | 3.92 (0.96) | 4.14 (3.71) | 5.19 (1.85) | 8.76 (2.24) | 9.62 (1.23) | 7.62 (2.17) |
| Workable Time (seconds) | | 236 | 25 | 241 | 95 | 30 | 37 | 33 | 23 | 15 |

Comparing with the case where any primer was used, when the primer 1 was used, adhesion strengths to both enamel and dentin became higher and workable times were within a proper range.

By comparing the primer 1 with the primers 2, 3, 4 and 5, it was found that lacking either of the component (h) barbituric acid or the component (i) amine reduced adhesion strength to both enamel and dentin.

Thereby, it is confirmed that both the component (h) barbituric acid and the component (i) amine are essential.

In addition, by comparing among the primer 1, the primer 6, the primer 2, the primer 7 and the primer 8, it was found that lacking both the component (h) barbituric acid and the component (i) amine (Primer 2) resulted in low adhesion strength and extremely long workable time, and that as the amounts of the above components was getting larger, adhesion strength to enamel became gradually lower and workable time became shorter. The primer 8 (10 weight % TMBA and 10 weight % DEPT) showed workable time which deviated from the acceptable range.

Thereby, it was confirmed that the respective appropriate ranges for the component (h) barbituric acid and the component (i) amine were 1 weight % to 5 weight %.

Example 3

Effects of Primer Formulation on Resin Cement Properties (2)

(1) Manufacture of Primer

Based on a formulation shown in Table 9, primers 9 to 16 consisting of a liquid I and a liquid II were manufactured.

In this Example, a sum of the components in the liquid I or the liquid II was set to 50 parts by weight with respect to the whole primer formulation, respectively. Additionally, the formulation of the liquid I was common for the primers.

TABLE 9

Formulation of Primer

| | | | Primers | | | | | | | |
|---|---|---|---|---|---|---|---|---|---|---|
| | | Ingredient | 9 | 10 | 11 | 12 | 13 | 14 | 15 | 16 |
| Liquid I (wt. %) | (e) | Distilled water | 37 | 37 | 37 | 37 | 37 | 37 | 37 | 37 |
| | (h) | TMBA | 3 | 3 | 3 | 3 | 3 | 3 | 3 | 3 |
| | (i) | DEPT | 3 | 3 | 3 | 3 | 3 | 3 | 3 | 3 |
| | (x) | Acetone | 7 | 7 | 7 | 7 | 7 | 7 | 7 | 7 |
| Liquid II (wt. %) | (f) | 6-MHPA | 7 | — | 7 | — | 2 | 5 | 10 | 7 |
| | (g) | 4-AET | 15 | — | — | 15 | 5 | 10 | 25 | — |
| | | 4-META | — | — | — | — | — | — | — | 15 |
| | (j) | 2-HEMA | 20 | 35 | 30 | 25 | 35 | 25 | 10 | 20 |
| | (k) | Acetone | 8 | 15 | 13 | 10 | 8 | 10 | 5 | 8 |

(2) Evaluation of Resin Cement Properties

[Adhesion Strength]

Tooth specimens (enamel and dentin) surface-treated with the primers 9 to 16 were used to measure adhesion strength of the resin cement 10 of the present invention. Results from measuring are listed in Table 10.

[Workable Time]

Tooth specimens (enamel and dentin) surface-treated with the primers 9 to 16 were used to measure workable time of the resin cement 10 of the present invention. Results from measuring are listed in Table 10.

TABLE 10

Evaluation of Properties for Resin Cement

| | | Primer | | | | | | | |
|---|---|---|---|---|---|---|---|---|---|
| Evaluated property | | 9 | 10 | 11 | 12 | 13 | 14 | 15 | 16 |
| Avg. (SD) of Adhesion Strength (MPa) | Enamel | 14.05 (2.18) | 9.08 (2.84) | 6.55 (2.22) | 10.68 (3.68) | 13.51 (3.24) | 13.08 (2.75) | 18.02 (2.80) | 18.54 (3.98) |
| | Dentin | 11.25 (2.68) | 4.56 (1.38) | 4.23 (0.94) | 5.74 (2.55) | 9.83 (2.19) | 9.05 (2.93) | 8.59 (2.33) | 8.13 (2.09) |
| Workable Time (seconds) | | 20 | 43 | 37 | 20 | 43 | 27 | 23 | 27 |

By comparing the primers 9 and 16 with the primers 10, 11 and 12, it was found that lacking either of the component (f) polymerizable monomer represented by the general formula (I) or the component (g) polymerizable monomer containing a dibasic acid carboxyl group or acid anhydride reduced adhesion strength to both enamel and dentin.

Thereby, it is confirmed that both the component (f) polymerizable monomer represented by the general formula (I) and the component (g) polymerizable monomer containing a dibasic acid carboxyl group or acid anhydride are essential.

In addition, by comparing among the primer 13, the primer 14, the primer 9 and the primer 15, it was found that all the primers resulted in good adhesion strength and good workability.

Thereby, it was confirmed that the appropriate content range for the component (f) polymerizable monomer represented by the general formula (I) was 2 weight % to 10 weight, and that of the component (g) polymerizable monomer containing a dibasic acid carboxyl group or acid anhydride was 5 weight % to 25 weight %.

Example 4

Effects of Primer Formulation on Resin Cement Properties (3)

(1) Manufacture of Primer

Based on a formulation shown in Table 11, primers 17 to 24 consisting of a liquid I and a liquid II were manufactured.

In this Example, a sum of the components in the liquid I or the liquid II was set to 50 parts by weight with respect to the whole primer formulation, respectively. Additionally, the formulation of the liquid I was common for the primers.

(2) Evaluation of Resin Cement Properties

[Adhesion Strength]

Tooth specimens (enamel and dentin) surface-treated with the Primers 17 to 24 were used to measure adhesion strength of the resin cement 10 of the present invention. Measurements of adhesion strength were performed at the initial stage and after accelerated aging test (2000 thermal cycles) in order to assess durability. Results from measuring are listed in Table 12.

[Workable Time]

Tooth specimens (enamel and dentin) surface-treated with the primers 17 to 24 were used to measure workable time of the resin cement 10 of the present invention. Results from measuring are listed in Table 12.

TABLE 11

Formulation of Primers

| | | Ingredient | 17 | 18 | 19 | 20 | 21 | 22 | 23 | 24 |
|---|---|---|---|---|---|---|---|---|---|---|
| Liquid I (wt. %) | (e) | Distilled water | 37 | 37 | 37 | 37 | 37 | 37 | 37 | 37 |
| | (h) | TMBA | 2 | 2 | 2 | 2 | 2 | 2 | 2 | 2 |
| | (i) | DEPT | 3 | 3 | 3 | 3 | 3 | 3 | 3 | 3 |
| | (x) | Acetone | 8 | 8 | 8 | 8 | 8 | | 8 | 8 |
| Liquid II (wt. %) | (f) | 6-MHPA | 7 | — | — | — | — | — | — | — |
| | | 6-MHPP | — | 7 | — | — | — | — | — | — |
| | | 5-MPPA | — | — | 7 | — | — | — | — | — |
| | | 5-MPPP | — | — | — | 7 | — | — | — | — |
| | | 10-MDPA | — | — | — | — | 7 | — | — | — |
| | | 10-MDPP | — | — | — | — | — | 7 | — | — |
| | | 2-MEPA | — | — | — | — | — | — | 7 | — |
| | | 2-MEPP | — | — | — | — | — | — | — | 7 |
| | (g) | 4-AET | 15 | 15 | 15 | 15 | 15 | 15 | 15 | 15 |
| | (j) | 2-HEMA | 20 | 20 | 20 | 20 | 20 | 20 | 20 | 20 |
| | (k) | Acetone | 8 | 8 | 8 | 8 | 8 | 8 | 8 | 8 |

TABLE 12

Evaluation of Properties for Resin Cement

| | | | | | Primer | | | | |
|---|---|---|---|---|---|---|---|---|---|
| Evaluated property | | 17 | 18 | 19 | 20 | 21 | 22 | 23 | 24 |
| Avg. (SD) of Adhesion Strength (MPa) | Enamel | 16.64 (2.84) | 16.03 (3.20) | 15.70 (2.12) | 16.11 (2.56) | 15.84 (1.89) | 13.68 (3.02) | 10.76 (2.28) | 11.20 (1.17) |
| | Dentin | 8.72 (2.24) | 9.32 (2.59) | 10.02 (2.05) | 9.65 (3.02) | 8.22 (2.61) | 7.59 (2.05) | 8.07 (1.52) | 9.60 (1.45) |
| Avg. (SD) of Adhesion Strength After Aging (MPa) | Enamel | 12.05 (2.60) | 11.34 (3.47) | 11.21 (2.12) | 13.08 (1.77) | 8.33 (0.75) | 12.04 (2.57) | 5.02 (1.45) | 4.32 (1.28) |
| | Dentin | 7.81 (1.77) | 8.89 (2.02) | 9.05 (1.96) | 8.87 (1.45) | 8.01 (2.11) | 8.12 (1.98) | 3.71 (1.10) | 2.02 (0.21) |
| Workable Time (seconds) | | 37 | 25 | 27 | 37 | 25 | 27 | 20 | 30 |

By comparing the primers 17 to 22 with the primers 23, and 24, it was found that equivalent adhesion strength and workability were obtained at the initial stage and that the primers 23 and 24 showed significantly reduced adhesion strengths after the accelerated aging test.

Thereby, it is confirmed that the appropriate range for the carbon numbers of $R^2$ in the component (f) polymerizable monomer represented by the general formula (I) was 5 to 10.

Example 5

Effects of Resin Cement Formulation on Resin Cement Properties (1)

(1) Manufacture of Resin Cement

Based on a formulation shown in Table 13, two-paste type resin cements 11 to 15 consisting of a paste A and a paste B were manufactured.

In this Example, each of sums of the components other than the component (d) life time stabilizer in the paste A and the paste B was set to 50 parts by weight and an appropriate amount of the component (d) was added in the respective pastes.

TABLE 13

Formulation of Resin Cement (parts by weight)

| Paste | | Ingredient | Resin Cement | | | | |
|---|---|---|---|---|---|---|---|
| | | | 11 | 12 | 13 | 14 | 15 |
| A | (a) | UDMA | 10.5 | 10.5 | 10.5 | 10.5 | 10.5 |
| | | 3G | 5.0 | 5.0 | 5.0 | 5.0 | 5.0 |
| | (b) | FASG filler | 33.1 | 33.3 | 33.3 | 33.1 | 33.1 |
| | (b') | R-974 | 1.0 | 1.0 | 1.0 | 1.0 | 1.0 |
| | (c)-(2) | BBA•Na | 0.2 | — | 0.2 | 0.2 | 0.2 |
| | (c)-(4) | DEPT | 0.2 | 0.2 | — | 0.2 | 0.2 |
| | (d) | BHT | 0.01 | 0.01 | 0.01 | 0.01 | 0.01 |
| B | (a) | Bis-GMA | 10.7 | 10.7 | 10.7 | 10.7 | 10.7 |
| | | 3G | 5.0 | 5.0 | 5.0 | 5.0 | 5.0 |
| | (b) | FASG filler | 33.1 | 33.1 | 33.1 | 33.2 | 33.2 |
| | (b') | R-711 | 1.0 | 1.0 | 1.0 | 1.0 | 1.0 |
| | (c)-(1) | BPO | 0.1 | 0.1 | 0.1 | — | 0.1 |
| | (c)-(3) | CQ | 0.1 | 0.1 | 0.1 | 0.1 | — |
| | (d) | BHT | 0.05 | 0.05 | 0.05 | 0.05 | 0.05 |

(2) Evaluation of Resin Cement Properties

[Adhesion Strength]

Tooth specimens (enamel and dentin) surface-treated with the primer 1 were used to measure adhesion strength of the resin cements 11 to 15. Results from measuring are listed in Table 14.

[Flexural Strength]

Flexural strengths for the resin cements 11 to 15 were measured. Results from measuring are listed in Table 14.

[Curing Time]

Curing times for the resin cements 11 to 15 were measured. Results from measuring are listed in Table 14.

[Workable Time]

Tooth specimens (enamel and dentin) surface-treated with the primer 1 were used to measure workable time of the resin cements 11 to 15. Results from measuring are listed in Table 14.

TABLE 14

Evaluation of Properties for Resin Cement

| Evaluated property | | Resin Cement | | | | |
|---|---|---|---|---|---|---|
| | | 11 | 12 | 13 | 14 | 15 |
| Avg. (SD) of Adhesion Strength (MPa) | Enamel | 17.97 (3.09) | 8.12 (2.09) | 14.59 (4.52) | 17.93 (5.27) | 13.69 (4.34) |
| | Dentin | 13.97 (3.09) | 8.87 (1.11) | 9.80 (1.17) | 5.95 (1.25) | 7.52 (1.34) |
| Avg. (SD) of Flexural Strength (MPa) | | 111.60 (6.31) | 120.94 (12.76) | 10.63 (1.83) | 89.00 (13.13) | 67.16 (13.97) |
| Curing Time (seconds) | | 211 | 253 | over 1 hour | over 1 hour | 188 |
| Workable Time (seconds) | | 25 | 20 | 22 | 90 | 20 |

By comparing the resin cement 11 with the resin cements 12 and 13, it was found that lacking the component (c)-(2) salt of barbituric acid in the paste A reduced adhesion strength and lacking the component (c)-(4) amine extremely lengthened the curing time and extremely reduced flexural strength, resulting in insufficient cure.

Thereby, it is confirmed that both the component (c)-(2) salt of barbitutic acid and the component (c)-(4) amine were essential as components of resin cement.

By comparing Resin cement 11 with Resin cements 14 and 15, it was found that lacking the component (c)-(1) organic peroxide in Paste B extremely lengthened the curing time and reduced adhesion strength to enamel and dentin and flexural strength, resulting in insufficient cure and that lacking the component (c)-(3) photopolymerization initiator reduced adhesion strength to dentin and flexural strength.

Example 6

Effects of Resin Cement Formulation on Resin Cement Properties (2)

(1) Manufacture of Resin Cement

Based on a formulation shown in Table 15, two-paste type resin cements 16 to 20 consisting of a paste A and a paste B were manufactured.

In this Example, each of sums of the components other than the component (d) life time stabilizer in the paste A and the paste B was set to 50 parts by weight and an appropriate amount of the component (d) was added in the respective pastes. Additionally, the formulation of the paste B was common for the respective resin cements.

TABLE 15

Formulation of Resin Cement (parts by weight)

| Paste | | Ingredient | Resin Cement | | | | |
|---|---|---|---|---|---|---|---|
| | | | 16 | 17 | 18 | 19 | 20 |
| A | (a) | Bis-GMA | 10.5 | 10.5 | 10.5 | 10.5 | 10.5 |
| | | 3G | 5.0 | 5.0 | 5.0 | 5.0 | 5.0 |
| | (b) | FASG filler | 32.7 | 32.6 | 32.3 | 31.8 | 30.8 |
| | (b') | R-974 | 1.55 | 1.55 | 1.55 | 1.55 | 1.55 |
| | (c)-(2) | TMBA•Na | 0.1 | 0.2 | 0.5 | 1.0 | 2.0 |
| | (c)-(4) | DEPT | 0.15 | 0.15 | 0.15 | 0.15 | 0.15 |
| | (d) | BHT | 0.01 | 0.01 | 0.01 | 0.01 | 0.01 |
| B | (a) | UDMA | 10.2 | 10.2 | 10.2 | 10.2 | 10.2 |
| | | 3G | 5.0 | 5.0 | 5.0 | 5.0 | 5.0 |
| | (b) | FASG filler | 33.1 | 33.1 | 33.1 | 33.1 | 33.1 |
| | (b') | R-711 | 1.5 | 1.5 | 1.5 | 1.5 | 1.5 |
| | (c)-(1) | BPO | 0.1 | 0.1 | 0.1 | 0.1 | 0.1 |

TABLE 15-continued

Formulation of Resin Cement (parts by weight)

| | | Resin Cement | | | | |
|---|---|---|---|---|---|---|
| Paste | Ingredient | 16 | 17 | 18 | 19 | 20 |
| (c)-(3) | CQ | 0.1 | 0.1 | 0.1 | 0.1 | 0.1 |
| (d) | BHT | 0.03 | 0.03 | 0.03 | 0.03 | 0.03 |

(2) Evaluation of Resin Cement Properties

[Adhesion Strength]

Tooth specimens (enamel and dentin) surface-treated with the primer 1 were used to measure adhesion strength of the resin cements 16 to 20. Results from measuring are listed in Table 16.

[Flexural Strength]

Flexural strengths for the resin cements 16 to 20 were measured. Results from measuring are listed in Table 16.

[Curing Time]

Curing times for the resin cements 16 to 20 were measured. Results from measuring are listed in Table 16.

[Workable Time]

Tooth specimens (enamel and dentin) surface-treated with the primer 1 were used to measure workable time of the resin cements 16 to 20. Results from measuring are listed in Table 16.

TABLE 16

Evaluation of Properties for Resin Cement

| | | Resin Cement | | | | |
|---|---|---|---|---|---|---|
| Evaluated property | | 16 | 17 | 18 | 19 | 20 |
| Avg. (SD) of Adhesion Strength (MPa) | Enamel | 15.30 (3.67) | 14.55 (1.72) | 16.29 (4.87) | 13.71 (1.50) | 14.52 (4.58) |
| | Dentin | 10.84 (1.98) | 10.64 (3.90) | 9.54 (0.87) | 12.01 (2.11) | 10.08 (1.02) |
| Avg. (SD) of Flexural Strength (MPa) | | 102.07 (15.11) | 112.50 (8.11) | 108.62 (9.15) | 105.17 (8.89) | 112.07 (5.50) |
| Curing Time (seconds) | | 229 | 224 | 208 | 217 | 198 |
| Workable Time (seconds) | | 22 | 22 | 25 | 22 | 34 |

By comparing the resin cements 16 to 20, it was found that all the resin cements were good in adhesion strength, flexural strength, curing time and workability.

Thereby, it was confirmed that the appropriate content range for the component (c)-(2) salt of barbituric acid was 0.1 to 2.0 parts by weight.

Example 7

Effects of Resin Cement Formulation on Resin Cement Properties (3

(1) Manufacture of Resin Cement

Based on a formulation shown in Table 17, two-paste type resin cements 21 to 25 consisting of a paste A and a paste B were manufactured.

In this Example, each of sums of the components other than the component (d) life time stabilizer in the paste A and the paste B was set to 50 parts by weight and an appropriate amount of the component (d) was added in the respective pastes. Additionally, the formulation of the paste B was common for the respective resin cements.

TABLE 17

Formulation of Resin Cement (parts by weight)

| | | | Resin Cement | | | | |
|---|---|---|---|---|---|---|---|
| Paste | Ingredient | | 21 | 22 | 23 | 24 | 25 |
| A | (a) | UDMA | 10.5 | 10.5 | 10.5 | 10.5 | 10.5 |
| | | 3G | 5.0 | 5.0 | 5.0 | 5.0 | 5.0 |
| | (b) | FASG filler | 32.7 | 32.6 | 32.3 | 31.8 | 30.8 |
| | (b') | R-974 | 1.5 | 1.5 | 1.5 | 1.5 | 1.5 |
| | (c)-(2) | BBA•Ca | 0.2 | 0.2 | 0.2 | 0.2 | 0.2 |
| | (c)-(4) | DEPT | 0.1 | 0.2 | 0.5 | 1.0 | 2.0 |
| | (d) | BHT | 0.01 | 0.01 | 0.01 | 0.01 | 0.01 |
| B | (a) | Bis-GMA | 10.2 | 10.2 | 10.2 | 10.2 | 10.2 |
| | | 3G | 5.0 | 5.0 | 5.0 | 5.0 | 5.0 |
| | (b) | FASG filler | 33.1 | 33.1 | 33.1 | 33.1 | 33.1 |
| | (b') | R-711 | 1.5 | 1.5 | 1.5 | 1.5 | 1.5 |
| | (c)-(1) | BPO | 0.1 | 0.1 | 0.1 | 0.1 | 0.1 |
| | (c)-(3) | CQ | 0.1 | 0.1 | 0.1 | 0.1 | 0.1 |
| | (d) | BHT | 0.03 | 0.03 | 0.03 | 0.03 | 0.03 |

(2) Evaluation of Resin Cement Properties

[Adhesion Strength]

Tooth specimens (enamel and dentin) surface-treated with the primer 1 were used to measure adhesion strength of the resin cements 21 to 25. Results from measuring are listed in Table 18.

[Flexural Strength]

Flexural strengths for the resin cements 21 to 25 were measured. Results from measuring are listed in Table 18.

[Curing Time]

Curing times for the resin cements 21 to 25 were measured. Results from measuring are listed in Table 18.

[Workable Time]

Tooth specimens (enamel and dentin) surface-treated with the primer 1 were used to measure workable time of the resin cements 21 to 25. Results from measuring are listed in Table 18.

TABLE 18

Evaluation of Properties for Resin Cement

| | | Resin Cement | | | | |
|---|---|---|---|---|---|---|
| Evaluated property | | 21 | 22 | 23 | 24 | 25 |
| Avg. (SD) of Adhesion Strength (MPa) | Enamel | 13.30 (2.38) | 14.55 (3.53) | 18.74 (1.87) | 15.77 (3.78) | — |
| | Dentin | 12.04 (3.27) | 13.68 (3.68) | 12.93 (1.01) | 9.22 (2.22) | — |
| Avg. (SD) of Flexural Strength (MPa) | | 108.87 (9.21) | 112.65 (10.08) | 114.08 (10.96) | — | — |
| Curing Time (seconds) | | 326 | 234 | 181 | 108 | — |
| Workable Time (seconds) | | 22 | 22 | 20 | 18 | — |

Remark:
The symbol "—" indicates that values could not be measured.

By comparing the resin cements 21 to 25, it was found that increasing the content of the component (c)-(4) amine shortened curing time and workable time and that neither adhesion strength nor flexural strength could be sufficiently obtained.

Additionally, data for the flexural strength of the resin cement 24 could not be measured due to its short curing time. Data for the adhesion strength, flexural strength, curing time and workable time of the Resin cement 25 could not be measured due to its short curing time and workable time.

Thereby, it was confirmed that the appropriate content range for the component (c)-(4) amine was 0.1 to 0.5 parts by weight.

Example 8

Effects of Resin Cement Formulation on Resin Cement Properties (4)

(1) Manufacture of Resin Cement

Based on a formulation shown in Table 19, two-paste type resin cements 26 to 30 consisting of a paste A and a paste B were manufactured.

In this Example, each of sums of the components other than the component (d) life time stabilizer in the paste A and the paste B was set to 50 parts by weight and an appropriate amount of the component (d) was added in the respective pastes. Additionally, the formulation of the paste A was common for the respective resin cements.

TABLE 19

Formulation of Resin Cement (parts by weight)

| Paste | | Ingredient | Resin Cement | | | | |
|---|---|---|---|---|---|---|---|
| | | | 26 | 27 | 28 | 29 | 30 |
| A | (a) | UDMA | 10.5 | 10.5 | 10.5 | 10.5 | 10.5 |
| | | 3G | 5.0 | 5.0 | 5.0 | 5.0 | 5.0 |
| | (b) | FASG filler | 32.7 | 32.7 | 32.7 | 32.7 | 32.7 |
| | (b') | R-974 | 1.5 | 1.5 | 1.5 | 1.5 | 1.5 |
| | (c)-(2) | TMBA•Na | 0.3 | 0.3 | 0.3 | 0.3 | 0.3 |
| | (c)-(4) | DEPT | 0.1 | 0.1 | 0.1 | 0.1 | 0.1 |
| | (d) | BHT | 0.01 | 0.01 | 0.01 | 0.01 | 0.01 |
| B | (a) | Bis-GMA | 10.2 | 10.2 | 10.2 | 10.2 | 10.2 |
| | | 3G | 5.0 | 5.0 | 5.0 | 5.0 | 5.0 |
| | (b) | FASG filler | 33.1 | 33.0 | 32.7 | 32.5 | 32.2 |
| | (b') | R-974 | 1.5 | 1.5 | 1.5 | 1.5 | 1.5 |
| | (c)-(1) | BPO | 0.1 | 0.2 | 0.5 | 0.7 | 1.0 |
| | (c)-(3) | CQ | 0.1 | 0.1 | 0.1 | 0.1 | 0.1 |
| | (d) | BHT | 0.03 | 0.05 | 0.05 | 0.05 | 0.05 |

(2) Evaluation of Resin Cement Properties

[Adhesion Strength]

Tooth specimens (enamel and dentin) surface-treated with the primer 1 were used to measure adhesion strength of the resin cements 26 to 30. Results from measuring are listed in Table 20.

[Flexural Strength]

Flexural strengths for the resin cements 26 to 30 were measured. Results from measuring are listed in Table 20.

[Curing Time]

Curing times for the resin cements 26 to 30 were measured. Results from measuring are listed in Table 20.

[Workable Time]

Tooth specimens (enamel and dentin) surface-treated with the primer 1 were used to measure workable time of the resin cements 26 to 30. Results from measuring are listed in Table 20.

TABLE 20

Evaluation of Properties for Resin Cement

| Evaluated property | | Resin Cement | | | | |
|---|---|---|---|---|---|---|
| | | 26 | 27 | 28 | 29 | 30 |
| Avg. (SD) of Adhesion Strength (MPa) | Enamel | 16.01 (4.25) | 18.52 (3.81) | 18.26 (2.36) | 19.59 (3.01) | 19.59 (3.01) |
| | Dentin | 10.27 (3.45) | 10.03 (1.27) | 14.30 (2.01) | 13.45 (2.70) | 16.04 (4.53) |
| Avg. (SD) of Flexural Strength (MPa) | | 114.23 (9.68) | 109.56 (8.89) | 112.23 (9.51) | 111.42 (9.09) | — |
| Curing Time (seconds) | | 375 | 204 | 224 | 105 | 72 |
| Workable Time (seconds) | | 25 | 22 | 22 | 17 | 10 |

Remark:
The symbol "—" indicates that values could not be measured.

By comparing the resin cements 26 to 30, it was found that increasing the content of the component (c)-(1) organic peroxide resulted in sufficient adhesion strength but shortened curing time and workable time.

Thereby, it was confirmed that the appropriate content range for the component (c)-(1) organic peroxide was 0.1 to 0.5 parts by weight.

What is claimed is:

1. A kit comprising:
   a water-free two-paste dental composite resin cement comprising:
   20.0 to 45.0 parts by weight of a component (a) radical polymerizable monomer;
   50.0 to 80.0 parts by weight of a component (b) fluoroaluminosilicate glass filler;
   0.1 to 0.5 parts by weight of a component (c)-(1) organic peroxide;
   0.1 to 2.0 parts by weight of a component (c)-(2) alkali metal salt or an alkaline earth metal salt of barbituric acid;
   0.05 to 1.0 parts by weight of a component (c)-(3) photopolymerization initiator;
   0.1 to 0.5 parts by weight of a component (c)-(4) aromatic secondary or tertiary amine; and
   0.02 to 0.2 parts by weight of a component (d) shelf life stabilizer, based on 100 parts by weight of the whole resin cement formulation, provided that a sum of the respective components does not exceed 100 parts by weight; and
   a dental primer comprising:
   20.0 to 60.0 weight % of a component (e) water;
   2.0 to 10.0 weight % of a component (f) polymerizable monomer represented by the general formula (I):

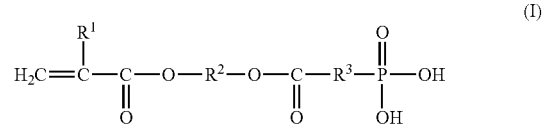

wherein $R^1$ is a hydrogen atom or a methyl group, $R^2$ is an alkylene group having a carbon number of 5 to 10, $R^3$ is an alkylene group having a carbon number of 1 to 6;

5.0 to 25.0 weight % of a component (g) polymerizable monomer containing a dibasic acid carboxyl group or acid anhydride;

1.0 to 5.0 weight % of a component (h) barbituric acid; and 1.0 to 5.0 weight % of a component (i) amine, based on 100 weight % of the whole primer formulation, provided that a sum of the respective components does not exceed 100 weight %.

2. The kit according to claim 1, which further comprises 50.0 weight % or lower of a component (j) polymerizable compound containing a hydroxide group.

3. The kit according to claim 1, which further comprises weight % or lower of a component (k) organic solvent.

4. The kit according to claim 1, wherein the dental primer is a two-liquid type.

\* \* \* \* \*